(12) United States Patent
Torrens Jover et al.

(10) Patent No.: US 8,492,425 B2
(45) Date of Patent: Jul. 23, 2013

(54) 5-METHYL-1-(NAPHTHALEN-2-YL)-1H-PYRAZOLES USEFUL AS SIGMA RECEPTOR INHIBITORS

(75) Inventors: Antoni Torrens Jover, Barcelona (ES); Maria Rosa Cuberes-Altisent, Barcelona (ES); Maria Jose Pretel Sanchez, Barcelona (ES); Maria Magdalena Bordas Gelabert, Barcelona (ES)

(73) Assignee: Laboratories Del Dr. Esteve, S.A., Barcelona (ES)

( * ) Notice: Subject to any disclaimer, the term of this patent is extended or adjusted under 35 U.S.C. 154(b) by 157 days.

(21) Appl. No.: 12/988,929

(22) PCT Filed: Apr. 27, 2009

(86) PCT No.: PCT/EP2009/055065
§ 371 (c)(1),
(2), (4) Date: Dec. 28, 2010

(87) PCT Pub. No.: WO2009/130331
PCT Pub. Date: Oct. 29, 2009

(65) Prior Publication Data
US 2011/0118253 A1    May 19, 2011

(30) Foreign Application Priority Data

Apr. 25, 2008   (EP) .................................. 08384005

(51) Int. Cl.
*A61K 31/415*   (2006.01)
*C07D 231/22*   (2006.01)

(52) U.S. Cl.
USPC ........................................ 514/407; 548/370.1

(58) Field of Classification Search
None
See application file for complete search history.

(56) References Cited

FOREIGN PATENT DOCUMENTS

| EP | 1829875 A1 | 9/2007 |
|---|---|---|
| WO | 2006021462 A1 | 3/2006 |
| WO | 2007098953 A1 | 9/2007 |

OTHER PUBLICATIONS

Walker et al., "Sigma Receptors: Biology and Function", Pharmacological Reviews, vol. 42, No. 4, pp. 355-402, 1990.
Goodman and Gilman's "The Pharmacologcal Basis of Therapeutics", 8th Ed, pp. 13-18.
Kim et al., "Reexamination of the Aqueous-Chemistry of N-Nitroso-3-hydroxymorpholine, a Metabolite of the Carcinogen N-Nitrosomorpholine", Chem. Res. Toxicol, 16(6), pp. 715-720; 2003.
Effenberger et al., "Synthesen mit β-Äthoxy-acrylsäurechloriden", Chem. Ber., 102 (10), pp. 3260-3267, 1969.
DeHaven-Hudkins et al., "Characterization of the binding of [3H](+)-pentazocine to σ recognition sites in guinea pig brain", Eur. J. Pharmacol., 227, pp. 371-378 1992.
International Search Report for PCT/EP2009/05565, dated Aug. 21, 2009.

*Primary Examiner* — Kamal Saeed
(74) *Attorney, Agent, or Firm* — Hoffman & Baron, LLP

(57) ABSTRACT

The invention relates to compounds having the formula (I):

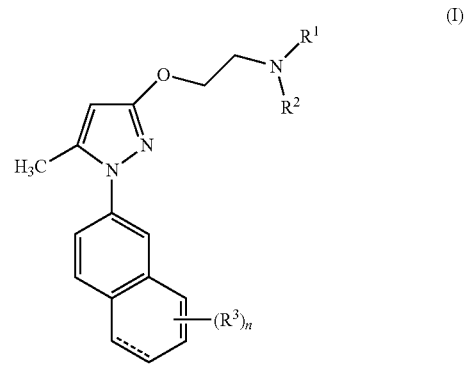

wherein the dashed line (represented by - - - ) represents an optional double bond;
$R^1$ is hydrogen and $R^2$ is hydroxyethyl; or $R^1$ and $R^2$ together with the nitrogen atom to which they are attached form a morpholinyl ring optionally substituted with one or two hydroxy groups;
each $R^3$ is independently hydroxy or $C_{1-6}$alkoxy;
n is selected from 0, 1, and 2;
or a N-oxide, salt, prodrug, solvate or stereoisomer thereof;
with the proviso that the compound where the dashed line represents a double bond, $R^1$ and $R^2$ together with the nitrogen atom to which they are attached form a morpholinyl ring, and n is 0, is excluded.
Also provided are methods for the preparation of compounds of formula (I); their uses as a medicaments, particularly for the treatment or prophylaxis of a sigma receptor mediated diseases or conditions.

8 Claims, No Drawings

5-METHYL-1-(NAPHTHALEN-2-YL)-1H-PYRAZOLES USEFUL AS SIGMA RECEPTOR INHIBITORS

CROSS-REFERENCE TO RELATED APPLICATIONS

This application is the National Stage of International Application No. PCT/EP2009/055065, filed Apr. 27, 2009, which claims the benefit of European Application No. EP08384005.8, filed Apr. 25, 2008, the contents of which are incorporated by reference herein.

FIELD OF THE INVENTION

The present invention concerns compounds having inhibitory activity on sigma receptors. It concerns further to compositions comprising these compounds as active ingredients, as well as processes for preparing these compounds and compositions.

BACKGROUND OF THE INVENTION

Psychiatric and neurologic disorders are among the most severe and chronic diseases and conditions. These disorders are also extremely difficult to treat effectively because of the multiplicity of the symptoms and etiologies.

Amongst the therapeutic arsenal to combat these psychiatric and neurologic disorders, sigma receptor—inhibitors have been found useful in the treatment of psychosis and movement disorders such as dystonia and tardive dyskinesia, and motor disturbances associated with Huntington's chorea or Tourette's syndrome and in Parkinson's disease (Walker, J. M. et al, *Pharmacological Reviews*, 1990, 42, 355).

WO2006021462 and WO2007098953 describe pyrazole-containing compounds having pharmacological activity towards the sigma receptor, useful in the therapy of pain, in general, and, more particularly, in treatment of neuropathic pain or allodynia. These compounds have the following chemical structure:

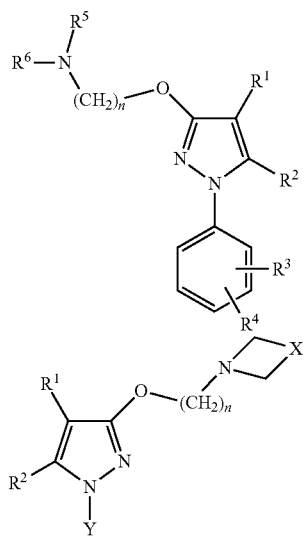

WO200027394 discloses activators of soluble guanylate cyclase (sGC) having a pyrazole ring.

In spite of this background, there is still a need in the art to provide alternative pyrazole-containing compounds having pharmacological activity towards the sigma receptor, useful in the therapy of pain, in general, and more particularly, in the treatment of neuropathic pain or allodynia.

Likewise, it would be highly desirable to provide new sigma receptor inhibitors which are superior to others known in the art in one or more of the following pharmacological related properties: potency, increased affinity for sigma receptors, enhanced analgesic effect, decreased cytotoxicity, improved pharmacokinetics, acceptable dosage, and pill burden, for example.

SUMMARY OF THE INVENTION

The present invention relates to compounds having the formula (I):

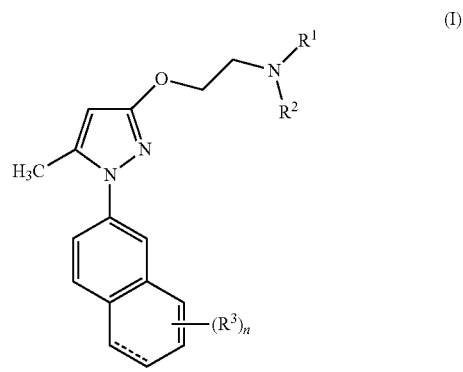

wherein the dashed line (represented by - - - ) represents an optional double bond;
$R^1$ is hydrogen and $R^2$ is hydroxyethyl; or $R^1$ and $R^2$ together with the nitrogen atom to which they are attached form a morpholinyl ring optionally substituted with one or two hydroxy groups;
each $R^3$ is independently hydroxy or $C_{1-6}$alkoxy;
n is selected from 0, 1, and 2;
or an N-oxide, salt, prodrug, solvate or stereoisomer thereof;
with the proviso that the compound where the dashed line represents a double bond, $R^1$ and $R^2$ together with the nitrogen atom to which they are attached form a morpholinyl ring, and n is 0, is excluded.

The invention further relates to methods for the preparation of the compounds of formula (I), their N-oxides, their salts, prodrugs, quaternary amines, metal complexes, solvates and stereochemically isomeric forms thereof, their intermediates, and the use of the intermediates in the preparation of the compounds of formula (I).

One objective of the invention relates to compounds of formula (I) per se, their N-oxides, their salts, prodrugs, quaternary amines, metal complexes, solvates and stereochemically isomeric forms thereof, for their use as medicaments.

Another further objective of this invention relates to pharmaceutical compositions comprising a pharmaceutically acceptable carrier and a pharmaceutically effective amount of a compound of formula (I), as specified herein.

The invention further relates to the aforementioned pharmaceutical composition for administration to a subject suffering from a sigma receptor mediated disease or condition.

An additional objective of the invention relates to the use of a compound of formula (I), or a N-oxide, salt, prodrug, quaternary amine, metal complex, solvate or stereochemically isomeric forms thereof, for the manufacture of a medicament for the treatment or prophylaxis of a sigma receptor mediated disease or condition.

Another further objective of this invention relates to a method for the treatment or prophylaxis of a sigma receptor mediated disease or condition in a warm-blooded animal, said method comprising the administration of an effective amount of a compound of formula (I), or a N-oxide, salt, prodrug, quaternary amine, metal complex, solvate or stereochemically isomeric forms thereof.

DETAILED DESCRIPTION OF THE INVENTION

One embodiment of the present invention relates to a compound having the formula (I):

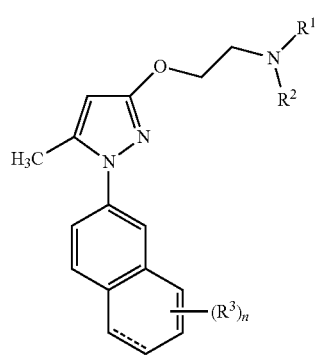

(I)

wherein the dashed line (represented by - - - ) represents an optional double bond;
$R^1$ is hydrogen and $R^2$ is hydroxyethyl; or $R^1$ and $R^2$ together with the nitrogen atom to which they are attached form a morpholinyl ring optionally substituted with one or two hydroxy groups;
each $R^3$ is independently hydroxy or $C_{1-6}$alkoxy;
n is selected from 0, 1, and 2;
or an N-oxide, salt, prodrug, solvate or stereoisomer thereof;
with the proviso that the compound where the dashed line represents a double bond, $R^1$ and $R^2$ together with the nitrogen atom to which they are attached form a morpholinyl ring, and n is 0, is excluded.

The following definitions apply to the terms used herein unless otherwise noted.

As used herein $C_{1-4}$alkyl, as a group or part of a group, defines straight or branched chain saturated hydrocarbon radicals having from 1 to 4 carbon atoms such as methyl, ethyl, propyl, 1-methylethyl, butyl; $C_{1-6}$alkyl, as a group or part of a group, defines straight or branched chain saturated hydrocarbon radicals having from 1 to 6 carbon atoms such as the group defined for $C_{1-4}$alkyl and pentyl, hexyl, and 2-methylbutyl.

The term $C_{1-6}$alkoxy means $C_{1-6}$alkyloxy or a $C_{1-6}$alkyl ether radical, wherein the term $C_{1-6}$alkyl is as defined above. Examples of suitable alkyl ether radicals include methoxy, ethoxy, n-propoxy, isopropoxy, n-butoxy, iso-butoxy, sec-butoxy, tert-butoxy, and hexanoxy.

In the compounds of formula (I) or subgroups thereof, the substituent —$R^3$ may be bonded to any carbon atom of the naphthyl or the 5,6-dihydronaphthalenyl ring, for example, the substituent —$R^3$ may be bonded to any one of carbon atoms 1, 3, 4, 5, 6, 7, or 8, as depicted hereafter:

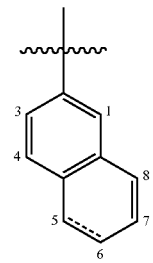

It should be noted that the radical positions on any molecular moiety used in the definitions may be anywhere on such moiety as long as it is chemically stable.

Radicals used in the definitions of any variable herein include all possible isomers unless otherwise indicated. For instance, pentyl includes 1-pentyl, 2-pentyl and 3-pentyl.

When any variable occurs more than one time in any constituent, each definition is independent.

Whenever used herein, the term "compounds of formula (I)", or "the present compounds" or similar terms, is meant to include the compounds of formula (I), their N-oxides, salts, prodrugs, quaternary amines, metal complexes, solvates and stereochemically isomeric forms. One embodiment of this invention comprises compounds of formula (I) or any subgroup of compounds of formula (I) specified herein, as well as their N-oxides and salts in their possible stereoisomeric forms. Another embodiment of this invention comprises compounds of formula (I) or any subgroup of compounds of formula (I) specified herein, as well as their salts in their possible stereoisomeric forms.

The compounds of formula (I) may have several centers of chirality and may exist as stereochemically isomeric forms. The term "stereoisomers" or "stereochemically isomeric forms", as used herein, define all possible variants of the compounds of formula (I) made up of the same atoms bonded by the same sequence of bonds, but having different three-dimensional structures, and which are not interchangeable.

In particular, those compounds of formula (I) wherein
the dashed line (represented by - - - ) is not present, i.e. there is no double bond resulting in a 5,6-dihydronaphthalenyl ring in compound of formula (I), and $R^3$ is bonded to carbon atoms 5, 6, or 5 and 6; or
$R^1$ and $R^2$ together with the nitrogen atom to which they are attached form a morpholinyl ring substituted with one or two hydroxy groups;
do have at least one center of chirality.

With reference to the instances where (R) or (S) is used to designate the absolute configuration of a chiral atom within a substituent, the designation is done taking into consideration the whole compound and not the substituent in isolation.

Unless otherwise mentioned or indicated, the chemical designation of a compound encompasses the mixture of all possible stereochemically isomeric forms, which said compound may possess. Said mixture may contain all diastereomers and/or enantiomers of the basic molecular structure of said compound. All stereochemically isomeric forms of the compounds of the present invention, both in pure or mixed form, are intended to be comprised within the scope of the present invention.

Pure stereoisomeric forms of the compounds and intermediates, as mentioned herein, are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular, having a stereoisomeric excess of 94% up to 100% and, most in particular, having a stereoisomeric excess of 97% up to 100%. The terms "enantiomerically pure" and "diastereomerically pure" should be understood in a similar way, but taking into account to the enantiomeric excess, and the diastereomeric excess, respectively, of the mixture in question.

Pure stereoisomeric forms of the compounds and intermediates of this invention may be obtained by the application of procedures known in the art. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. If a specific stereoisomer is desired, said compound will be synthesized preferably by stereospecific methods of preparation. These methods will advantageously employ enantiomerically pure starting materials.

The compounds of formula (I) may be obtained as racemic mixtures of enantiomers which can be separated from one another following art-known resolution procedures. The racemic compounds of formula (I) may be converted into their corresponding diastereomeric salt forms by reaction with a suitable chiral acid. Said diastereomeric salt forms could be separated subsequently, for example, by selective or fractional crystallization, and the product enantiomers liberated by alkali or acid. An alternative manner of separating the enantiomeric forms of the compounds of formula (I) involves liquid chromatography, in particular, liquid chromatography using a chiral stationary phase. Said pure stereochemically isomeric forms may also be derived from the corresponding pure stereochemically isomeric forms of the appropriate starting materials, provided that the reaction occurs stereospecifically. If a specific stereoisomer is desired, said compound may be synthesized preferably by stereospecific methods of preparation. These methods may advantageously employ enantiomerically pure starting materials.

The diastereomeric racemates of the compounds of formula (I) can be obtained separately by conventional methods. Appropriate physical separation methods that may advantageously be employed are, for example, selective crystallization and chromatography, e.g. column chromatography.

For some of the compounds of formula (I), their N-oxides, salts, solvates, prodrugs, quaternary amines, or metal complexes, and the intermediates used in the preparation thereof, the absolute stereochemical configuration was not experimentally determined. A person skilled in the art is able to determine the absolute configuration of such compounds using known methods such as, for example, X-ray diffraction.

Some of the compounds of formula (I) and intermediates thereof may also exist in their tautomeric form. Such forms, although not explicitly indicated in the above formula, are intended to be included within the scope of the present invention.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

The phrase "pharmaceutically acceptable" refers to molecular entities and compositions that do not produce adverse, allergic, or other untoward reactions when administered to an animal or a human.

The term "prodrug", as used throughout this text, means pharmacologically acceptable derivatives of a compound, such as esters, amides and phosphates, such that the resulting in vivo biotransformation product of the derivative is the active drug as defined in the compounds of formula (I). The reference by Goodman and Gilman (The Pharmacological Basis of Therapeutics, 8th ed, McGraw-Hill, Int. Ed. 1992, "Biotransformation of Drugs", p 13-15) describing prodrugs generally is hereby incorporated. Preferably, prodrugs should have excellent aqueous solubility, increased bioavailability and be readily metabolized into active inhibitors in vivo. Prodrugs of a compound according to the present invention may be prepared by modifying functional groups present in the compound in such a way that the modifications are cleaved, either by routine manipulation or in vivo, to the parent compound.

Pharmaceutically acceptable ester prodrugs, which are hydrolysable in vivo and derived from those compounds of formula (I) having a hydroxy or a carboxyl group, are preferred according to the present invention. An in vivo hydrolysable ester is an ester, which is hydrolysed in the human or animal body, to produce the parent acid or alcohol. Suitable pharmaceutically acceptable esters for carboxy include $C_{1-6}$alkoxymethyl esters for example methoxy-methyl, $C_{1-6}$alkanoyloxymethyl esters for example pivaloyloxymethyl, phthalidyl esters, $C_{3-8}$cycloalkoxycarbonyloxy$C_{1-6}$ alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyl-oxyethyl which may be formed at any carboxy group in the compounds of this invention.

An in vivo hydrolysable ester of a compound of the formula (I), containing a hydroxy group, includes inorganic esters such as phosphate esters and α-acyloxyalkyl ethers and related compounds, that as a result of the in vivo hydrolysis of the ester breakdown to give the parent hydroxy group. Examples of α-acyloxyalkyl ethers include acetoxy-methoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

The term "salt" as mentioned herein is meant to comprise any stable salts, which the compounds of formula (I) are able to form, and preferably, non-toxic pharmaceutically acceptable salts. Salts that are not pharmaceutically acceptable are also encompassed within the scope of the present invention, since they refer to intermediates that are useful in the preparation of compounds with pharmacological activity. The salts can be conveniently obtained by treating the base form with the appropriate acids such as inorganic acids, like for example, hydrohalic acids, e.g. hydrochloric, hydrobromic; sulfuric acid; nitric acid; phosphoric acid; or organic acids, like for instance, acetic, propanoic, hydroxyacetic, 2-hydroxypropanoic, 2-oxopropanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzene-sulfonic, cyclohexanesulfamic, 2-hydroxybenzoic, and 4-amino-2-hydroxybenzoic. Conversely, the salt form can be converted by treatment with alkali into the free base form.

The compounds of formula (I) containing an acidic proton may also be converted into their non-toxic metal or amine addition salt forms by treatment with the appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, and lysine.

The term salts is also meant to include the hydrates or solvates which the compounds of formula (I) are able to form, including, e.g. the alcoholates, such as methanolates or ethanolates. The term "solvate" refers to crystal forms of the compounds of formula (I) that contain either stoichiometric or non-stoichiometric amounts of solvent. Since water is a solvent, solvates also include hydrates. The term "pseudopolymorph" is synonym to solvate since it applies to polymorphic crystalline forms that have solvent molecules incorporated in their lattice structures. Examples of solvates are hydrates and alcoholates, such as methanolates or ethanolates.

The term "quaternary amine" as used herein defines the quaternary ammonium salts which the compounds of formula (I) are able to form by reaction between a basic nitrogen of a compound of formula (I) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen.

Pharmaceutically acceptable counterions include chloro, bromo, iodo, trifluoroacetate and acetate. The counterion of choice can be introduced using ion exchange resins.

It will be appreciated that the compounds of formula (I) may have metal binding, chelating, complex forming properties and therefore may exist as metal complexes or metal chelates. Such metalated derivatives of the compounds of formula (I) are intended to be included within the scope of the present invention.

The N-oxide forms of the present compounds are meant to comprise the compounds of formula (I) wherein one or several nitrogen atoms are oxidized to the so-called N-oxide. As such, a particular embodiment of the present invention relates to those compounds having the formula (Ib):

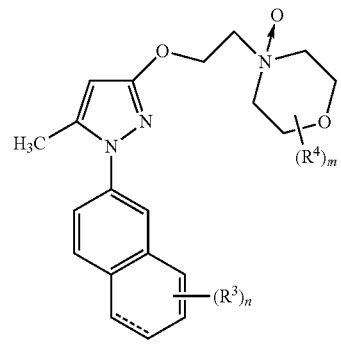

(Ib)

a salt, prodrug, solvate or stereoisomer thereof,
wherein the dashed line (represented by - - -) represents an optional double bond;
each $R^3$ is independently hydroxy or $C_{1-6}$alkoxy;
n is selected from 0, 1 and 2;
$R^4$ is hydroxy; and
m is selected from 0, 1, and 2.

Another embodiment of the present invention relates to those compounds having the formula (Ic):

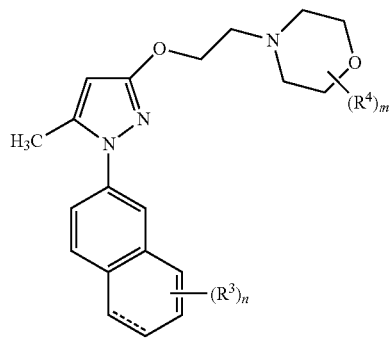

(Ic)

an N-oxide, salt, prodrug, solvate or stereoisomer thereof,
wherein the dashed line (represented by - - -) represents an optional double bond;
each $R^3$ is independently hydroxy or $C_{1-6}$alkoxy;
n is selected from 1 and 2;
$R^4$ is hydroxy; and
m is selected from 0, 1, and 2.

Another embodiment of the present invention relates to those compounds having the formula (Ic'):

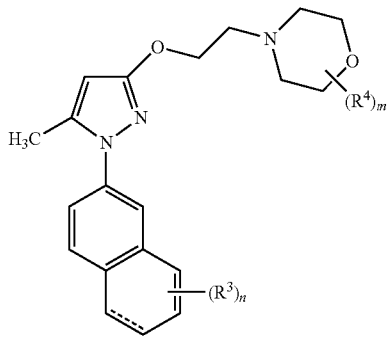

(Ic')

an N-oxide, salt, prodrug, solvate or stereoisomer thereof,
wherein the dashed line (represented by - - - ) represents an
optional double bond;

each $R^3$ is independently hydroxy or $C_{1-6}$ alkoxy;

n is selected from 0, 1 and 2;

$R^4$ is hydroxy; and m is selected from 1 and 2.

Another embodiment of the present invention relates to those compounds having the formula (Id):

(Id)

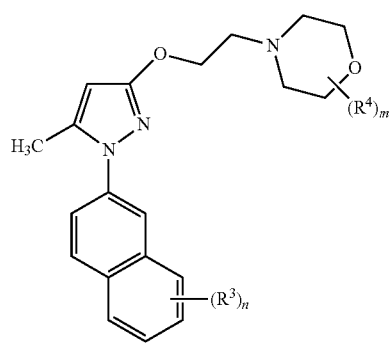

an N-oxide, salt, prodrug, solvate or stereoisomer thereof,
wherein each $R^3$ is independently hydroxy or $C_{1-6}$alkoxy;

n is selected from 1 and 2;

$R^4$ is hydroxy; and m is selected from 0, 1, and 2.

Another embodiment of the present invention relates to those compounds having the formula (Id'):

(Id')

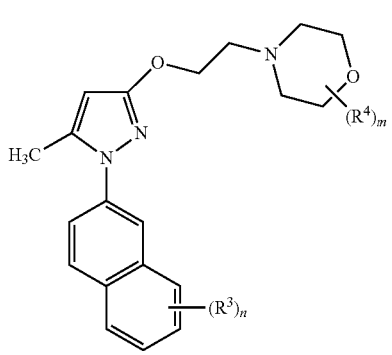

an N-oxide, salt, prodrug, solvate or stereoisomer thereof,
wherein each $R^3$ is independently hydroxy or $C_{1-6}$alkoxy;

n is selected from 0, 1 and 2;

$R^4$ is hydroxy; and m is selected from 1 and 2.

Another embodiment of the present invention relates to those compounds having the formula (Ie):

(Ie)

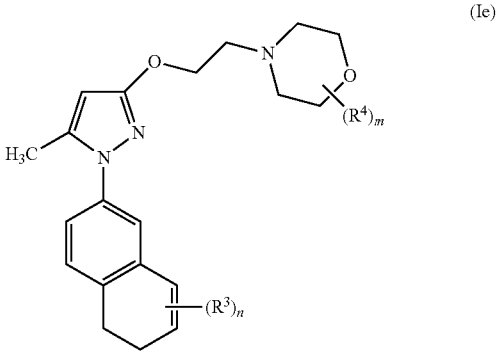

an N-oxide, salt, prodrug, solvate or stereoisomer thereof,
wherein each $R^3$ is independently hydroxy or $C_{1-6}$ alkoxy;

n is selected from 0, 1 and 2;

$R^4$ is hydroxy; and m is selected from 0, 1, and 2.

In compounds of formula (Ib), (Ic), (Ic'), (Id), (Id') and (Ie) the substituent —$R^4$ may be bonded to any carbon atom of the morpholinyl ring, i.e., the substituent —$R^4$ may be bonded to any one of carbon atoms 2, 3, 5, or 6, preferably to carbon atoms 2 or 6, as depicted hereafter:

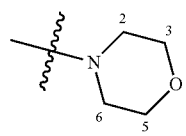

The compounds of formula (I) wherein $R_4$ is a hydroxyl group are chemically stable. Indeed, the stability of strain-free 6-membered cyclic hemiacetals and hemiaminals is well reported and there are different natural products possessing such moieties in their structures (for instance, glucose and many other aldoses exist as cyclic hemiacetals).

A further embodiment of the present invention relates to those compounds having the formula (If):

(If)

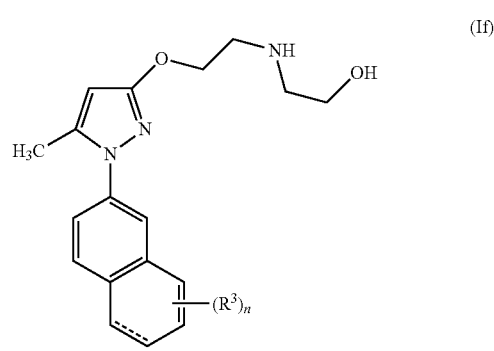

an N-oxide, salt, prodrug, solvate or stereoisomer thereof,
wherein
the dashed line (represented by - - - ) represents an optional double bond;

each R³ is independently hydroxy or C₁₋₆ alkoxy; and
n is selected from 0, 1, and 2.

A further embodiment of the present invention relates to those compounds having the formula (Ig):

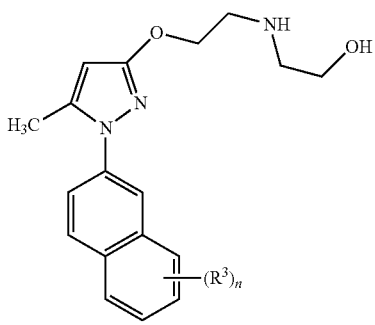

(Ig)

an N-oxide, salt, prodrug, solvate or stereoisomer thereof, wherein each R³ is independently hydroxy or C₁₋₆alkoxy; and
n is selected from 0, 1, and 2.

A further embodiment of the present invention relates to those compounds having the formula (Ih):

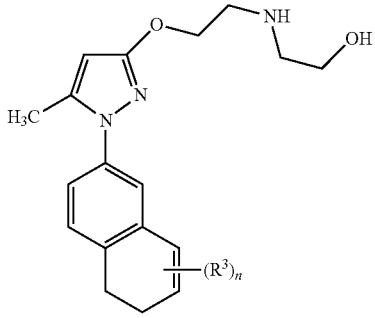

(Ih)

an N-oxide, salt, prodrug, solvate or stereoisomer thereof, wherein each R³ is independently hydroxy or C₁₋₆alkoxy; and
n is selected from 0, 1, and 2.

A further embodiment of the invention are those compounds of formula (I) or any of the subgroups thereof, wherein the naphthyl or the 5,6-dihydronaphthalenyl ring is substituted by R³ on positions 1, 3, 4, 5, 6, 7, or 8; preferably, on positions 5, 6, 7, or 8; more preferably, on positions 5, 6, or 7; by a hydroxy or a C₁₋₆alkoxy group, the latter preferably selected from a methoxy, ethoxy, n-propoxy, and isopropoxy, and more preferably, a methoxy group.

One embodiment of the present invention provides a process for preparing a compound of formula (I), wherein said process comprises:

a1) reacting a compound of formula (II) with a compound of formula (III) in a suitable solvent, and optionally in the presence of a catalyst and an aqueous solution of alkali, to obtain compound of formula (IV), which is further reacted with compound of formula (V) in a suitable solvent;

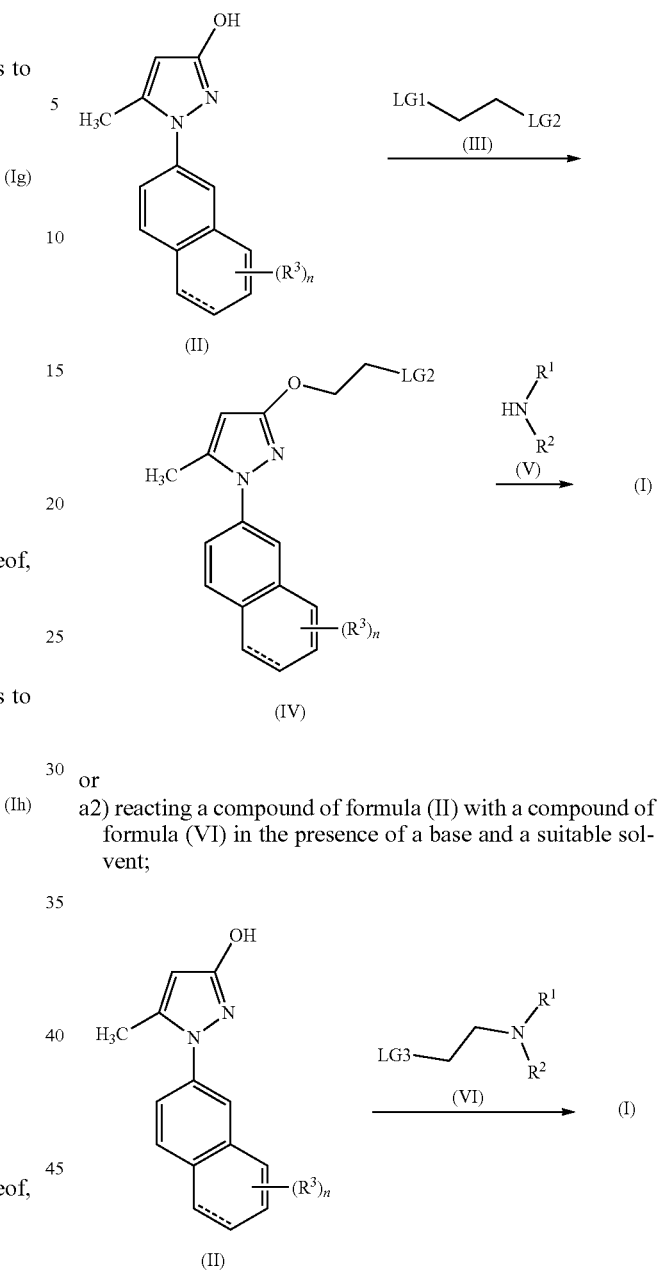

or a2) reacting a compound of formula (II) with a compound of formula (VI) in the presence of a base and a suitable solvent;

thereby obtaining compound of formula (I);
wherein in each of the compounds of formula (I), (II), (III), (IV), (V), and (VI), where applicable,
R¹, R², R³, and n are as defined above;
LG1, LG2, and LG3 represent each a leaving group.

Leaving groups LG1, LG2, and LG3 can be of a varied nature, known to a person skilled in the art. Preferably, they may be selected from a halide, e.g. bromide or chloride, or an arylsulfonyl group, e.g. mesylate, triflate, or tosylate.

In one embodiment of the invention, the reaction of (II) with (III) is a nucleophilic substitution where LG1 is a better leaving group than LG2 in the sense that when attacked by the oxygen atom, it shall leave first when compared to LG2. The power of leaving groups in leaving a particular molecule is known to those skilled in the art, e.g. bromide is a better leaving group than chloride. This reaction is conducted in a reaction-inert suitable solvent, such as hydrocarbons like toluene; halogenated hydrocarbons, e.g. dichloromethane, chloroform; dipolar aprotic solvents, such as acetonitrile, N,N-dimethylformamide (DMF), N,N-dimethylacetamide (DMA), dimethylsulfoxide (DMSO), hexamethylphosphoric triamide (HMPT); ethers, such as tetrahydrofuran (THF), and mixtures thereof with water.

In a particular embodiment of the invention, the reaction between compound of formula (II) with a compound of formula (III) is carried out in the presence of a catalyst, preferably, a phase transfer catalyst, such as a quaternary ammonium salt like tetrabutylammonium chloride, triethylbenzylammonium chloride, tri-n-octylmethylammonium chloride, trimethyldecylammonium chloride, tetramethylammonium bromide, and tetraethylammonium bromide, or a phosphonium salt, using an aqueous solution of alkali, such as an aqueous solution of sodium bicarbonate, or an aqueous solution of sodium hydroxide.

The resulting compound of formula (IV) is further reacted with compound of formula (V) in a reaction-inert suitable solvent as indicated above. The nucleophilic attack results in compound of formula (I).

Compounds of formula (III), such as 1-bromo-2-chloroethane, are easily available from commercial suppliers, like Sigma-Aldrich.

In the following list, there are provided different compounds of formula (V), which are easily prepared with either commercial products or literature references:
- morpholine, from Sigma-Aldrich.
- 2-aminoethanol, from Sigma-Aldrich.
- 2-hydroxymorpholine, from *Journal of Heterocyclic Chemistry*, 1981, 18(4), 825-8.
- 3-hydroxymorpholine, from Kim, H. J., Fishbein, J. C. *Chem. Res. Toxicol.* 2003, 16(6), 715-720.

In another embodiment of the invention, a compound of formula (I) may be prepared by reacting a compound of formula (II) with (VI) in the presence of a base which is strong enough to detract a hydrogen from the hydroxy group of the pyrazoline ring, like for example, an alkali of alkaline metal hydride, such as lithium hydride or sodium hydride, or an alkali metal alkoxide, such as sodium or potassium methoxide or ethoxide, potassium tert-butoxide, or potassium carbonate, triethylamine, pyridine, sodium iodide or cesium carbonate, in the presence of a reaction-inert suitable solvent, such as a dipolar aprotic solvent, e.g. DMF, DMA, DMSO or N-methylpyrrolidone. The resulting alcoholate is reacted with (VI), wherein LG3 is a suitable leaving group as mentioned above.

Intermediates of formula (II) may be obtained as described in WO2006021462 and WO2007098953, which are incorporated herein by reference, by reacting a acetohydrazide derivative with an ethyl acetoacetate; by reacting an hydrazine derivative with an ethyl butynoate; or by the method provided by F. Effenberger and W. Hartmann, *Chem. Ber.*, 102(10), 3260-3267, 1969, where an ethoxy-acrylic acid hydrazide is reacted with concentrated mineral acid.

According to the method provided in WO2006021462 and WO2007098953, an optionally substituted naphthalen-2-ylhydrazine, or an optionally substituted (5,6-dihydronaphthalen-2-yl)hydrazine, drawn both in the scheme below as a compound of formula (IX), or a salt thereof, is reacted with acetic anhydride in the presence of a suitable solvent, such as toluene. Subsequently, the resulting acetohydrazide derivative (X) is reacted with ethyl acetoacetate in the presence of phosphorus trichloride to cyclise and obtain a compound of formula (II). The optionally substituted naphthalen-2-ylhydrazine, the optionally substituted (5,6-dihydronaphthalen-2-yl)hydrazine, or a salt thereof, i.e. those compounds represented by formula (IX), may be obtained from an optionally substituted 2-nitronaphthalene or an optionally substituted 7-nitro-1,2-dihydronaphthalene, represented both by formula (VII), which is reduced to the corresponding amino derivative (VIII) by methods generally known by a person skilled in the art. The resulting amino moiety in compound of formula (VIII) is further oxidized with e.g. sodium nitrite in the presence of hydrogen chloride to form the diazonium salt, which is subsequently reduced with the aid of a reducing agent such as SnCl$_2$, or sodium sulfite in the presence of sodium hydroxide, thereby obtaining the optionally substituted naphthalen-2-ylhydrazine, or the optionally substituted (5,6-dihydronaphthalen-2-yl)hydrazine of formula (IX).

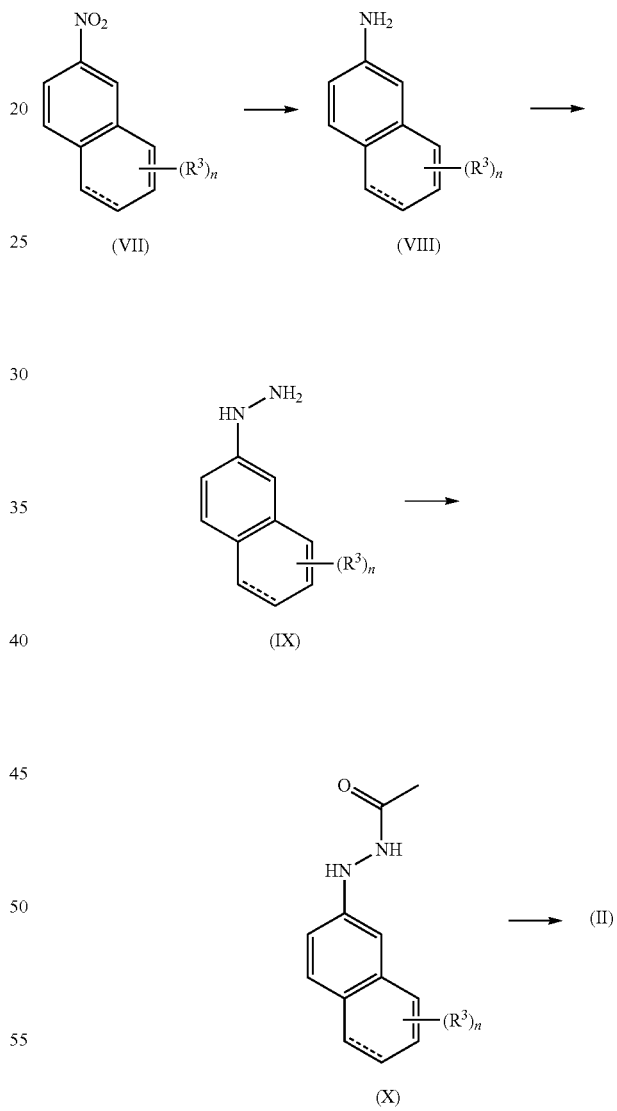

It should be noted that a compound of formula (II) could present a tautomeric form, i.e. compound of formula (IIa) as depicted below. Both compounds of formula (II) and (IIa) are comprised within the scope of the present invention, in particular as intermediates of a compound of formula (I), and in the methods provided in the present invention for the preparation of a compound of formula (I).

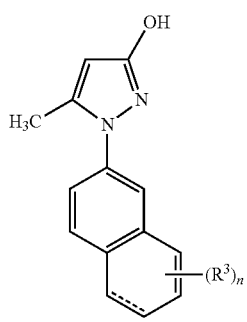

(II)

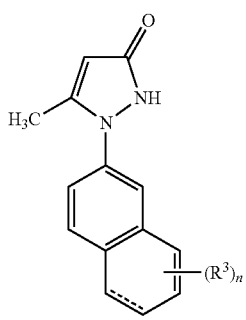

(IIa)

In the above-mentioned respective reactions, each of the obtained compounds, when necessary, can be collected from the reaction mixture according to the methods known in the art. For example, when insoluble materials are present, the desired compound can be obtained—after removing the insoluble materials by filtration—by removing the solvent, e.g. by removing the solvent under reduced pressure, and/or by adding water to the residue and extracting the mixture with a water-immiscible organic solvent such as ethyl acetate, etc. Optionally, the desired compound can be obtained after drying over anhydrous sodium sulfate, for instance, and further, if necessary, by purifying with any conventional method, such as recrystallization, column chromatography, or other techniques.

It is evident that in the foregoing and in the exemplified reactions, the reaction products may be isolated from the reaction medium and, if necessary, further purified by methods generally known in the art, such as extraction, crystallization and chromatography.

The different compounds comprised by formula (I) may be converted into each other following functional group transformation reactions well known in the art. Preferably, they are obtained by utilizing suitable starting materials, like for example, compounds of formula (II) including already the desired substituent $R^3$, or with compounds of formula (V) or (VI) including already the desired substituents $R^1$ and $R^2$.

In particular, in those compounds with hydroxy substitutents as $R^3$, such hydroxy moieties may be converted into the corresponding $C_{1-6}$ alkoxy by reacting the compounds with an $C_{1-6}$alkyl halide in the presence of a base, such as an alkali of alkaline metal hydride, like lithium hydride or sodium hydride, or an alkali metal alkoxide, like sodium or potassium methoxide or ethoxide, potassium tert-butoxide, or potassium carbonate, triethylamine, pyridine, sodium iodide, cesium carbonate, etc. The $C_{1-6}$alkyl halide may be selected, for instance, from methyl or ethyl iodide.

In addition, in those compounds with $C_{1-6}$alkoxy substitutents as $R^3$, such $C_{1-6}$alkoxy moieties may be converted into the corresponding hydroxy by submitting the relevant compounds to acidic conditions, such as with hydrochloric acid, hydrobromic acid, or hydroiodic acid.

The compounds of formula (I) of the present invention may be converted to the corresponding N-oxide forms following procedures known in the art for converting a trivalent nitrogen into its N-oxide form. The N-oxide forms of the present compounds are meant to comprise the compounds of formula (I) wherein one or several nitrogen atoms are oxidized to the so-called N-oxide. Said N-oxidation reaction may generally be carried out by reacting compound of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarbo-peroxoic acid or halo substituted benzenecarboperoxoic acid, e.g. 3-chlorobenzene-carboperoxoic acid, peroxoalkanoic acids, e.g. peroxoacetic acid, alkylhydroperoxides, e.g. tert-butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

In another embodiment, the present invention relates to those compounds of formula (IIb), per se,

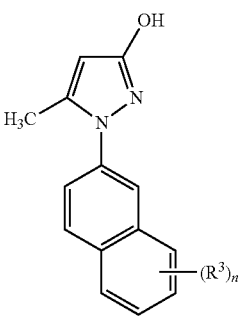

(IIb)

an N-oxide, salt, solvate or stereoisomer thereof, wherein, each $R^3$ is independently hydroxy or $C_{1-6}$alkoxy; and n is 2.

In another embodiment, the present invention relates to those compounds of formula (IIb'), per se,

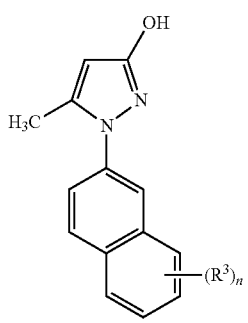

(IIb')

an N-oxide, salt, solvate or stereoisomer thereof, wherein, $R^3$ is hydroxy; and n is selected from 1 and 2.

In a further embodiment, the present invention relates to those compounds of formula (IIc), per se,

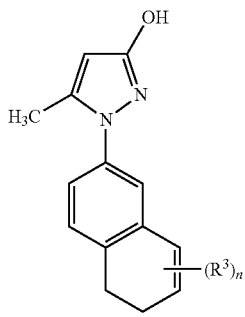
(IIc)

an N-oxide, salt, solvate or stereoisomer thereof, wherein,
each $R^3$ is independently hydroxy or $C_{1-6}$alkoxy; and
n is selected from 0, 1, and 2.

In yet another embodiment, the present invention relates to those compounds of formula (IV), per se,

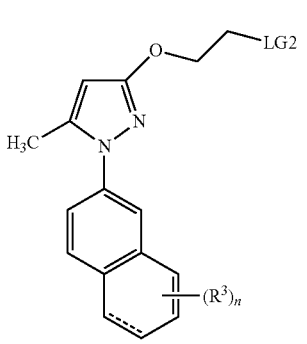
(IV)

an N-oxide, salt, solvate or stereoisomer thereof, wherein,
each $R^3$ is independently hydroxy or $C_{1-6}$alkoxy;
n is selected from 0, 1, and 2; and
LG2 represents a leaving group.

In a further embodiment, the invention refers to the use of the compounds of formula (II), (IIa), (IIb), (IIb'), (IIc), and (IV), each independently, as intermediates in the preparation of a compound of formula (I), pharmaceutically acceptable salts, isomers, prodrugs, and solvates thereof.

In a further aspect, the present invention concerns a pharmaceutical composition comprising a therapeutically effective amount of a compound of formula (I), and a pharmaceutically acceptable carrier. A therapeutically effective amount in this context is an amount sufficient to prophylactically act against, to stabilize or to treat a disease or condition mediated by a sigma receptor, in subjects suffering from such disease or condition. In still a further aspect, this invention relates to a process for preparing a pharmaceutical composition as specified herein, which comprises intimately mixing a pharmaceutically acceptable carrier with a therapeutically effective amount of a compound of formula (I).

Therefore, the compounds of the present invention may be formulated into various pharmaceutical forms for administration purposes. As appropriate compositions there may be cited all compositions usually employed for systemically administering drugs. To prepare the pharmaceutical compositions of this invention, an effective amount of the compounds of the present invention, optionally in a pharmaceutically acceptable salt or solvate thereof, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols, suspensions, syrups, elixirs, emulsions and solutions; or solid carriers, such as starches, sugars, kaolin, lubricants, binders, disintegrating agents, powders, pills, capsules, and tablets.

Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

The compounds of the present invention may also be administered via oral inhalation or insufflation by means of methods and formulations employed in the art for administration via this way. Thus, in general the compounds of the present invention may be administered to the lungs in the form of a solution, a suspension or a dry powder, a solution being preferred. Any system developed for the delivery of solutions, suspensions or dry powders via oral inhalation or insufflation are suitable for the administration of the present compounds.

Thus, the present invention also provides a pharmaceutical composition adapted for administration by inhalation or insufflation through the mouth comprising a compound of the present invention and a pharmaceutically acceptable carrier. The compounds of the present invention may be administered via inhalation of a solution in nebulized or aerosolized doses.

Depending on the mode of administration, the pharmaceutical composition will comprise, preferably, from 0.05 to 99% by weight, more preferably, from 0.1 to 70% by weight, or even more preferably, from 0.1 to 50% by weight of the active ingredient, and, from 1 to 99.95% by weight, more preferably, from 30 to 99.9% by weight, or even more preferably, from 50 to 99.9% by weight, of a pharmaceutically acceptable carrier, all percentages being based on the total composition weight.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions, and segregated multiples thereof.

The daily dosage of the compounds according to the invention will, of course, vary with the mode of administration, the treatment desired and the severity of the food intake disorder. However, in general, satisfactory results will be obtained when the compounds according to the invention are administered at a daily dosage in the range from 0.1 to 1000 mg/kg body weight, preferably from 1 to 1000 mg/kg, or more preferably, from 10 to 1000 mg/kg.

The compounds of the present invention are suitable for the prevention or treatment of a sigma receptor mediated disease or condition. They are particularly suitable in preventing or treating pain, neuropathic pain, inflammatory pain, or other pain conditions involving allodynia and/or hyperalgesia.

The compounds of the present invention, pharmaceutically acceptable salts, solvates thereof may therefore be used as a medicament. Said use as a medicament or method of treatment comprises the systemic administration to subjects in need thereof of an amount effective to combat a sigma receptor mediated disease or condition, in particular to treat or prevent pain, neuropathic pain, inflammatory pain, or other pain conditions involving allodynia and/or hyperalgesia.

The present invention also relates to the use of the presents compounds in the manufacture of a medicament for the treatment or the prevention of sigma receptor mediated diseases or conditions, particularly pain, neuropathic pain, inflammatory pain, or other pain conditions involving allodynia and/or hyperalgesia.

The present invention furthermore relates to a method of preventing or treating sigma receptors mediated diseases or conditions in a warm-blooded animal, said method comprising the administration of an effective amount of a compound of the present invention, pharmaceutically acceptable salts or solvates thereof.

The following examples are intended to illustrate the present invention and not to limit it thereto.

EXAMPLES

Example 1

4-{2-[1-(6-hydroxynaphthalen-2-yl)-5-methyl-1H-pyrazol-3-yloxy]ethyl}morpholine chlorhydrate 1.-2,5-dimethyl-2-(6-methoxynaphthalen-2-yldiazenyl) furan-3(2H)-one To a suspension of 2-amino-6-methoxynaphthalene (2.6 g, 15 mmol) in $H_2O$ (40 ml), HCl conc. was added (8 ml), it was cooled in an ice bath and a $NaNO_2$ solution (1.19 g, 17.3 mmol) in $H_2O$ (18 ml) was added dropwise shaking the mixture at 0° C. during 30 minutes.

The previous solution was diluted in $H_2O$ (80 ml), 2,5-dimethylfuran-2,3-dihydrofuran-3-one (1.94 g, 17.3 mmol) was added and was left shaking during 2 hrs at room temperature resulting in a yellow precipitate. It was filtered, washed with water and dried. It was thereby obtained 2,5-dimethyl-2-(6-methoxynaphthalen-2-yldiazenyl)furan-3-one (4.22 g, 95%) in a solid crude form of an ocre-yellow color that was used directly in the following synthesis step.

$^1$H-NMR (300 MHz, $CDCl_3$) δ ppm: 8.35 (s, 1H), 7.85 (d, J=8.8 Hz, 1H), 7.75-7.7 (m, 2H), 7.2 (m, 2H), 5.55 (s, 1H), 3.95 (s, 3H), 2.45 (s, 3H), 1.75 (s, 3H).

2.-3-hydroxy-5-methyl-1-(6-methoxynaphthalen-2-yl)-1H-pyrazole 2,5-dimethyl-2-(6-methoxynaphthalen-2-yldiazenyl)furan-3-one (4.2 g, 14.19 mmol) was added dropwise disolved in acetic acid (30 ml) over a mixture of acetic acid (20 ml) and hydrochloric acid approx. 6N (10 ml) and was heated at a temperature of 60° C. The mixture was kept shaking at 60° C. during 2 hours. The solution was cooled off, was added over a mixture of water/ice (400 ml) and the resulting solid was filtered and washed with water. It was dried and 1.66 g of crude solid remained, which were purified by chromatography in a silica gel column (eluting with AcOEt/petroleum ether 1/3 until 1/1). 0.49 g of a brown solid were obtained.

The previous filtering waters were diluted with more water and another precipitate was obtained that once dried, it weighed 0.43 g.

0.92 g of 3-hydroxy-5-methyl-1-(6-metoxynaphthalen-2-yl)-1H-pyrazol were obtained (yield: 26%), which was used directly in the following synthesis step.

$^1$H-NMR (300 MHz, $CDCl_3$) δ ppm: 7.8 (d, J=8.8 Hz, 1H), 7.75 (d, J=8.9 Hz, 1H), 7.7 (d, J=1.8 Hz, 1H), 7.5 (dd, J=2.2 Hz, J'=8.65 Hz, 1H), 7.2 (dd, J=2.4 Hz, J'=8.9 Hz, 1H), 7.15 (d, J=2.3 Hz, 1H), 5.6 (s, 1H), 3.95 (s, 3H), 2.3 (s, 3H).

3.-3-(2-chloroethoxy)-5-methyl-1-(6-methoxynaphthalen-2-yl)-1H-pyrazol

A mixture of 3-hydroxy-5-methyl-1-(6-methoxynaphthalen-2-yl)-1H-pyrazol (0.48 g, 1.9 mmol), 1-bromo-2-chloroethane (1.1 g, 7.6 mmol), aqueous solution of NaOH 40% (10 ml), toluene (10 ml), and tetraethylammonium bromide (catalytic quantity) was heated to reflux, with energic shaking, during 5 hrs. It was cooled, the phases were separated, the organic phase was washed several times with water, it was dried over $Na_2SO_4$, filtered, and evaporated to dryness, thereby obtaining 391 mg of a crude oil that was purified by means of chromatography in a column over silica gel (eluent: petroleum ether/ethyl acetate 10/0 until 9/1). 170 mg were recovered (28%) of 3-(2-chloroethoxy)-5-methyl-1-(6-methoxynaphthalen-2-yl)-1H-pyrazol in an orange-coloured oil.

$^1$H-NMR (300 MHz, $CDCl_3$) δ ppm: 7.75-7.65 (m, 3H), 7.45 (dd, J=2.1 Hz, J'=8.7 Hz, 1H), 7.1 (m, 2H), 5.65 (s, 1H), 4.45 (t, J=5.8 Hz, 2H), 3.85 (s, 3H), 3.8 (t, J=5.8 Hz, 2H), 2.25 (s, 3H).

4.-4-{2-[1-(6-methoxynaphthalen-2-yl)-5-methyl-1H-pyrazol-3-yloxy]ethyl}morpholine A solution of 3-(2-chloroethoxy)-5-methyl-1-(6-methoxynaphthalen-2-yl)-1H-pyrazol (0.63 g, 2 mmol) and morpholine (0.96 g, 8 mmol) in dimethylformamide (10 ml) was heated to 95° C., in a nitrogen atmosphere, during 20 hrs. Next, it was cooled, the DMF was evaporated in a rotavapor and water and dichloromethane was added to the residue. The organic phase was washed with water and, subsequently, it was extracted with HCl 2N several times. The collection of acidic waters was basified by the addition of NaOH 20% and it was extracted with dichloromethane, which was dried over $Na_2SO_4$, filtered and evaporated, thereby leaving a residue of 448 mg of 4-{2-[1-(6-methoxynaphthalen-2-yl)-5-methyl-1H-pyrazol-3-yloxy]ethyl}morpholine (yield: 61%) in the form of a colourless oil.

Purity determined by HPLC: 93.2%

$^1$H-NMR (300 MHz, $CDCl_3$) δ ppm: 7.8 (m, 3H), 7.55 (dd, J=1.9 Hz, J'=8.8 Hz, 1H), 7.15 (m, 2H), 5.7 (s, 1H), 4.35 (m, 2H), 3.95 (s, 3H), 3.75 (m, 4H), 2.8 (t, J=5.6 Hz, 2H), 2.6 (m, 4H), 2.3 (s, 3H).

5.-4-{2-[1-(6-hydroxynaphthalen-2-yl)-5-methyl-1H-pyrazol-3-yloxy]ethyl}morpholine chlorhydrate A solution of 4-{2-[1-(6-methoxynaphthalen-2-yl)-5-methyl-1H-pyrazol-3-yloxy]ethyl}morpholine (448 mg, 1.22 mmol) in HCl conc. (5 ml) was heated to reflux during 7 hrs, it was cooled and evaporated to dryness in a rotavapor. 375 mg of 4-{2-[1-(6-hydroxynaphthalen-2-yl)-5-methyl-1H-pyrazol-3-yloxy]ethyl}morpholine chlorhydrate were obtained in amorphous solid form that was highly hygroscopic (yield: 79%)

$^1$H-NMR (300 MHz, CD$_3$OD) δ ppm: 7.8 (m, 3H), 7.45 (dd, J=1.9 Hz, J'=8.8 Hz, 1H), 7.15 (m, 2H), 5.85 (s, 1H), 4.55 (m, 2H), 4.0 (m, 2H), 3.75 (m, 2H), 3.6 (m, 4H), 3.3 (solvent+m, 2H), 2.3 (s, 3H).

Example 2

4-{2-[1-(5-hydroxynaphthalen-2-yl)-5-methyl-1H-pyrazol-3-yloxy]ethyl}morpholine 2-amino-5-methoxynaphthalene A solution of commercially available 2-amino-5-hydroxynaphthalene (5.16 g, 31.48 mmol) in dimethylformamide (125 ml) was cooled with ice in an inert nitrogen atmosphere. Subsequently, NaH (1.39 g dispersion in a mineral oil at 60%, 34.6 mmoles) was added keeping the temperature below 10° C. and was shaken during 15 min. at ≈5° C. Subsequently methyl iodide (4.47 g, 31.48 mmol) solved in dimethylformamide (5 ml) was added and was left stirring at room temperature during 20 hrs. Water was added and it was evaporated to dryness in a rotavapor. To the remaining residue, water and ethylic ether were added. The aqueous phase was newly extracted with ether and the collection of organic phases was dried over Na$_2$SO$_4$, filtered, and evaporated to dryness. To the resulting crude slurry, a mixture of isopropylic alcohol/petroleum ether 1/1 was added, stirred during a few minutes and the insoluble precipitate was filtered. 4.21 g (77%) of 2-amino-5-methoxynaphthalene were obtained, with a purity determined by HPLC of 99%.

$^1$H-NMR (300 MHz, DMSO-d$_6$) δ ppm: 7.8 (d, J=8.8 Hz, 1H), 7.15 (m, 1H), 7.05 (m, 1H), 6.85 (dd, J=2.2 Hz, J'=8.9 Hz, 1H), 6.75 (d, J=2.2 Hz, 1H), 6.55 (d, J=7.5 Hz, 1H), 5.35 (bs, 2H), 3.85 (s, 3H).

(5-methoxynaphthalen-2-yl)hydrazine chlorhidrate

To a suspension of 2-amino-5-methoxynaphthalene (3.5 g, 20 mmol) in water (65 ml) and HCl conc. (25 ml) cooled down to −6° C., sodium nitrite (1.55 g, 22 mmol) in water (15 ml) was added dropwise. It was kept at stirring, approximately at the same temperature, during 45 minutes and subsequently a solution of SnCl$_2$ (9.3 g, 40 mmol) in HCl conc. (10 ml) was added. Once the addition was performed, it was allowed that the temperature would slowly increase until achieving room temperature, and it was filtered. The filtered solid was washed with water and ethylic ether and, subsequently, it was suspended in ethylic ether, with stirring, during a few minutes. It was filtered and dried resulting in 3.5 g of a crude brown solid, which was used directly in the following synthesis step.

$^1$H-NMR (300 MHz, DMSO-d$_6$) δ ppm: 10.3 (bs, 2H), 8.55 (bs, 1H), 8.0 (d, J=8.9 Hz, 1H), 7.35 (t, J=8.0 Hz, 1H), 7.25 (m, 1H), 7.2 (d, J=2.2 Hz, 1H), 7.1 (dd, J=2.3 Hz, J'=9.1 Hz, 1H), 6.8 (d, J=7.6 Hz, 1H), 3.95 (s, 3H).

N'-(5-methoxynaphthalen-2-yl)acetohydrazide

The hydrazine chlorhydrate (1.55 g, 6.9 mmol) was suspended in water (25 ml), K$_2$CO$_3$ (1 g) and ethyl acetate (25 ml) were added and it was energically shaken during 30 minutes. The phases were separated, the organic phase was washed with water, dried over Na$_2$SO$_4$, filtered, and evaporated to dryness resulting in 1.26 g of hydrazine base in a dark solid form. This solid was dissolved in anhydrous toluene (25 ml) and acetic anhydride (0.75 g, 7.4 mmol) was added keeping at stirring during 1 hr. Subsequently, petroleum ether was added and was left to rest in the fridge during 2 hrs. It was filtered and washed with more petroleum ether resulting, once dried, in 1.1 g (71%) of N'-(5-methoxynaphthalen-2-yl)acetohydrazide in the form of a reddish coloured solid, with a purity of 94% (HPLC).

3-hydroxy-5-methyl-1-(5-methoxynaphthalen-2-yl)-1H-pyrazol

To a mixture of N'-(5-methoxynaphthalen-2-yl)acetohydrazide (1.1 g, 4.75 mmol) and ethyl acetoacetate (0.75 g, 5.7 mmol), PCl$_3$ (0.65 g, 4.75 mmol) was added keeping at stirring. It was heated, with stirring, during 3.5 hrs at 55° C. It was cooled down to room temperature, water was added, it was stirred, and the insoluble solid was filtered, washing several times with water, and afterwards with ethylic ether. Once dried, 1.15 g of a greenish solid crude were obtained, which crystallized in ethyl acetate yielding 0.57 g of solid that was newly purified by means of chromatography in a silica gel column (eluent: petroleum ether/ethyl acetate, from 8/2 until 0/10) thereby obtaining 0.49 g (41%) of 3-hydroxy-5-methyl-1-(5-methoxynaphthalen-2-yl)-1H-pyrazole in the form of an earthy solid.

$^1$H-NMR (300 MHz, DMSO-d$_6$) δ 9.95 (s, 1H), 8.20 (d, J=9.1 Hz, 1H), 7.9 (d, J=2.1 Hz, 1H), 7.65 (dd, J=2.1 Hz, J'=9.1 Hz, 1H), 7.5 (m, 2H), 7.0 (d, J=7.5 Hz, 1H), 5.65 (s, 1H), 3.95 (s, 3H), 2.35 (s, 3H).

4-{2-[1-(5-methoxynaphthalen-2-yl)-5-methyl-1H-pyrazol-3-yloxy]ethyl}morpholine

To a solution of 3-hydroxy-5-methyl-1-(5-methoxynaphthalen-2-yl)-1H-pyrazol (150 mg, 0.59 mmol) in dimethylformamide (10 ml), 2-chloroethylmorpholine chlorhydrate (136 mg, 0.71 mmol), K$_2$CO$_3$ (245 mg, 1.77 mmol), and NaI (catalytic quantity) were added. The mixture was heated, in an inert nitrogen atmosphere, at 90° C. during 8 hrs. Subsequently it was cooled, filtered, and the filtered product was evaporated to dryness in a rotavapor. The residue was divided between water and ethylic ether. The organic phase was washed with water and afterwards with an aqueous solution of HCl 2N several times. The collection of the acidic aqueous phases were basified with a solution of NaOH 20% and it was extracted with ethyl acetate, which was washed with water, dried over sodium sulfate, filtered, and evaporated to dryness yielding 204 mg (94%) of 4-{2-[1-(5-methoxynaphthalen-2-yl)-5-methyl-1H-pyrazol-3-yloxy]ethyl}morpholine in the form of an oil.

$^1$H-NMR (300 MHz, DMSO-d$_6$): δ ppm 8.2 (d, J=9.1 Hz, 1H), 7.95 (d, J=2.2 Hz, 1H), 7.65 (dd, J=2.2 Hz, J'=9.1 Hz, 1H), 7.55 (m, 2H), 7.0 (d, J=7.3 Hz, 1H), 5.8 (s, 1H), 4.2 (t, J=5.7 Hz, 2H), 3.95 (s, 3H), 3.55 (m, 4H), 2.65 (t, J=5.7 Hz, 2H), 2.45 (m, 4H), 2.35 (s, 3H).

4-{2-[1-(5-hydroxynaphthalen-2-yl)-5-methyl-1H-pyrazol-3-yloxy]ethyl}morpholine chlorhydrate A solution of 4-{2-[1-(5-methoxynaphthalen-2-yl)-5-methyl-1H-pyrazol-3-yloxy]ethyl}morpholine (400 mg, 1.08 mmol) in HCl conc. (25 ml) was heated at 90° C. during 7 hrs, cooled down, and evaporated to dryness in a rotavapor. A remaining crude of 4-{2-[1-(5-hydroxynaphthalen-2-yl)-5-methyl-1H-pyrazol-3-yloxy]ethyl}morpholine chlorhydrate was left, which was crystallized in isopropyl alcohol-petroleum ether obtaining 0.32 g (76%) of the product in a solid amorphous form with a melting point m.p.<70° C., and highly hygroscopic.

$^1$H-NMR (300 MHz, DMSO-$d_6$) δ ppm: 10.5 (bs, 1H), 10.3 (s, 1H), 8.2 (d, J=9.1 Hz, 1H), 7.85 (d, J=1.9 Hz, 1H), 7.55 (dd, J=2.2 Hz, J'=9.1 Hz, 1H), 7.35 (m, 2H), 6.9 (dd, J=1.3 Hz, J'=6.9 Hz, 1H), 5.85 (s, 1H), 4.5 (m, 2H), 3.95 (m, 2H), 3.75 (t, J=12.1 Hz, 2H), 3.55-3.45 (m, 4H), 3.15 (m, 2H), 2.35 (s, 3H).

Example 3

4-{2-[1-(7-hydroxynaphthalen-2-yl)-5-methyl-1H-pyrazol-3-yloxy]ethyl}morpholine chlorhydrate 2,5-dimethyl-2-(7-methoxynaphthalen-2-yldiazenyl)furan-3(2H)-one To a suspension of 2-amino-7-methoxynaphthalene (5 g, 28.8 mmol) in $H_2O$ (72 ml), HCl conc. (14.5 ml) was added, it was then cooled down in an ice bath, and a solution of $NaNO_2$ (2.14 g, 31.1 mmol) in $H_2O$ (18 ml) was added dropwise maintaining the mixture at stirring at 0° C. during 30 minutes.

The previous solution was diluted with water (140 ml), 2,5-dimethyl-2,3-dihydrofuran-3-one (3.63 g, 31.4 mmol) was added and was left at stirring during 2 hrs at room temperature. It was then extracted with ethylic ether several times and the collection of organic phases was washed with water until a neutral pH was achieved, and it was dried over sodium sulfate. 6.8 g (80%) of 2,5-dimethyl-2-(7-methoxynaphthalen-2-yldiazenyl)furan-3-one were obtained in the form of a reddish coloured oil.

$^1$H-NMR (300 MHz, DMSO-$d_6$) δ ppm: 8.35 (d, J=1.9 Hz, 1H), 7.9 (dd, J=3.1 Hz, J'=9.0 Hz, 2H), 7.6 (d, J=2.6 Hz, 1H), 7.5 (dd, J=2.0 Hz, J'=8.8 Hz, 1H), 7.25 (dd, J=2.6 Hz, J'=8.9 Hz, 1H), 5.75 (s, 1H), 3.9 (s, 3H), 2.45 (s, 3H), 1.65 (s, 3H).

3-hydroxy-5-methyl-1-(7-methoxynaphthalen-2-yl)-1H-pyrazol 2,5-dimethyl-2-(7-methoxynaphthalen-2-yldiazenyl)furan-3-one (3.4 g, 11.48 mmol) dissolved in acetic acid (20 ml) was added dropwise over hydrochloric acid 6N (3.5 ml) and was heated to a temperature of 60° C. The mixture was kept stirring at 60° C. during 2 hours. The solution was cooled, poured over a mixture of water/ice (400 ml) and the solid precipitate was filtered and washed with water. It was dried and a solid crude remained, which was purified by means of crystallization in toluene, thereby resulting in 1.23 g (42%) of 3-hydroxy-5-methyl-1-(7-methoxynaphthalen-2-yl)-1H-pyrazol in the form of a white-greyish coloured solid.

$^1$H-NMR (300 MHz, DMSO-$d_6$) δ ppm: 9.95 (s, 1H), 7.85 (m, 3H), 7.4 (dd, J=2.1 Hz, J'=8.7 Hz, 1H), 7.35 (d, J=2.5 Hz, 1H), 7.15 (dd, J=2.5 Hz, J'=8.9 Hz, 1H), 5.6 (s, 1H), 3.85 (s, 3H), 2.35 (s, 3H).

4-{2-[1-(7-methoxynaphthalen-2-yl)-5-methyl-1H-pyrazol-3-yloxy]ethyl}morpholine chlorhydrate To a solution of 3-hydroxy-5-methyl-1-(7-methoxynaphthalen-2-yl)-1H-pyrazol (1.51 g, 5.96 mmol) in dimethylformamide (40 ml), cooled down to 0° C., a dispersion in mineral oil at 60% of NaH (0.36 g, 8.94 mmol) was added, the cooling bath was removed, and was left to stirring until it recovered the room temperature (1.5 hrs). Subsequently, 2-chloroethyl-morpholine (1.02 g, 6.85 mmol) dissolved in DMF (10 ml) was added dropwise, and the resulting mixture was heated at 60° C. during 20 hrs. Water-ice was added and it was evaporated to dryness in a rotavapor. The resulting slurry was divided between water and ethyl ether. The aqueous phase was newly extracted with a solvent, and the collection of organic phases was washed with water, dried over sodium sulfate, filtered, and evaporated yielding 2.19 g of a crude product, which was purified by crystallization of its chlorhydrate (prepared by dissolving in HCl-saturated dioxane) in isopropyl alcohol-ethyl ether. 1.78 g (74%) of the 4-{2-[1-(7-methoxynaphthalen-2-yl)-5-methyl-1H-pyrazol-3-yloxy]ethyl}morpholine chlorhydrate were obtained as a solid with a m.p.=143-147° C.

$^1$H-NMR (300 MHz, DMSO-$d_6$): δ ppm 10.9 (bs, 1H), 7.95-7.85 (m, 3H), 7.5 (dd, J=2.2 Hz, J'=8.8 Hz, 1H), 7.4 (d, J=2.6 Hz, 1H), 7.2 (dd, J=2.6 Hz, J'=8.9 Hz, 1H), 5.9 (s, 1H), 4.55 (m, 2H), 3.95 (m, 2H), 3.85 (s, 3H), 3.75 (t, J=11.7 Hz, 2H), 3.5 (m, 4H), 3.2 (m, 2H), 2.35 (s, 3H).

4-{2-[1-(7-hydroxynaphthalen-2-yl)-5-methyl-1H-pyrazol-3-yloxy]ethyl}morpholine chlorhydrate A solution of 4-{2-[1-(7-methoxynaphthalen-2-yl)-5-methyl-1H-pyrazol-3-yloxy]ethyl}morpholine chlorhydrate (1.3 g, 3.24 mmol) in HCl conc. (20 ml) was heated at 90° C. during 6 hrs, it was cooled down and evaporated to dryness in a rotavapor. The remaining crude oil was stirred with ethyl ether and the resulting solid precipitate was filtered; washed with more ethyl ether, and dried yielding 1.2 g (95%) of 4-{2-[1-(7-hydroxynaphthalen-2-yl)-5-methyl-1H-pyrazol-3-yloxy]ethyl}morpholine chlorhydrate in the form of a white solid with a m.p.=103-107° C.

$^1$H-NMR (DMSO-$d_6$) δ ppm: 10.8 (bs, 1H), 9.9 (bs, 1H), 7.85 (d, J=8.6 Hz, 1H), 7.8 (d, J=8.8 Hz, 1H), 7.75 (s, 1H), 7.4 (d, J=8.7 Hz, 1H), 7.2 (s, 1H), 7.1 (d, J=8.8 Hz, 1H), 5.85 (s, 1H), 4.55 (m, 2H), 3.95 (m+$H_2O$, 2H), 3.75 (t, J=11.9 Hz, 2H), 3.55-3.45 (m, 4H), 3.2 (m, 2H), 2.35 (s, 3H).

Example 4

6-(5-methyl-3-(2-morpholinoethoxy)-1H-pyrazol-1-yl)-1,2-dihydronaphthalene-1,2-diol The title compound is prepared using the process described in example 2 starting from 6-amino-1,2-dihydronaphthalene-1,2-diol instead of 2-amino-5-hydroxynaphthalene.

TABLE 1

| 500 and 125 MHz NMR data of compound nr. 1 according to Example 4 (m/z 372) (solv: MeOH-d4) | | |
|---|---|---|
| | $^1$H-NMR, ..δ.ppm | $^{13}$C-NMR, ..δ.ppm |
| 1 | — | 140.44 |
| 2 | 1H, 7.18, d (J = 2.1 Hz) | 123.72 |
| 2a | — | 135.15 |
| 3 | 1H, 6.48, dd (J = 9.8 and 2.2 Hz) | 127.76 |
| 4 | 1H, 6.03, dd (J = 9.8 and 2.6 Hz) | 133.84 |
| 5 | 1H, 4.40, dt (J = 10, 2.5 Hz) | 73.92 |
| 6 | 1H, 4.73, d (J = 10.1 Hz) | 75.36 |
| 6a | — | 138.03 |
| 7 | 1H, 7.64, d (J = 8.1 Hz) | 127.54 |

TABLE 1-continued 500 and 125 MHz NMR data of compound nr. 1
according to Example 4 (m/z 372) (solv: MeOH-d4)

|    | $^1$H-NMR, ..δ.ppm | $^{13}$C-NMR, ..δ.ppm |
|----|---|---|
| 8  | 1H, 7.29, dd (J = 8.0 and 2.1 Hz) | 124.92 |
| 9  | —  | 142.98 |
| 10 | 1H, 5.78, s | 93.79 |
| 11 | —  | 164.31 |
| 12 | 2H, 4.40, m | 66.04 |
| 13 | 2H, 3.15, m | 58.37 |
| 14 | 4H, 2.96 m | 54.58 |
| 15 | 4H, 3.80, t (J = 4.6 Hz) | 66.59 |
| 16 | 3H, 2.27, s | 12.82 |

Example 5

6-(3-(2-(2-Hydroxyethylamino)ethoxy)-5-methyl-1H-pyrazol-1-yl)naphthalen-2-ol hydrochloride 2-(2-(1-(6-Methoxynaphthalen-2-yl)-5-methyl-1H-pyrazol-3-yloxy)ethylamino)etanol

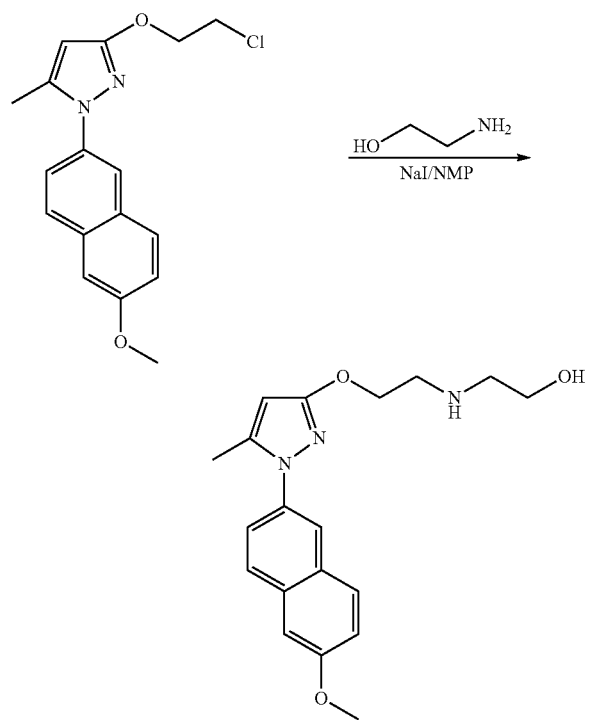

A mixture of 3-(2-chloroethoxy)-5-methyl-1-(6-methoxynaphthalen-2-yl)-1H-pyrazol (0.15 g, 0.47 mmol), ethanolamine (0.115 g, 1.89 mmol) and catalytic amount of NaI in N-methylpyrrolidone (NMP) (30 ml) was heated to 110° C., in a nitrogen atmosphere, during 20 hrs. Next, it was cooled, and water and ethyl acetate was added to the residue. The organic phase was washed with water several times, dried over $Na_2SO_4$, filtered and evaporated, thereby leaving a residue of 66 mg of 2-(2-(1-(6-Methoxynaphthalen-2-yl)-5-methyl-1H-pyrazol-3-yloxy)ethylamino)etanol. The aqueous phase was extracted with dichloromethane, dried over $Na_2SO_4$, filtered and evaporated leaving a crude residue, which was purified by a silica gel column chromatography (eluent: ethyl acetate/methanol, from 8/2 until 0/10) thereby obtaining additional 40 mg of desired compound. A total weight of 104 mg (yield: 65%) of 2-(2-(1-(6-methoxynaphthalen-2-yl)-5-methyl-1H-pyrazol-3-yloxy)ethylamino)etanol in the form of a colourless oil was obtained.

Purity determined by HPLC: 93.2%

$^1$H-NMR (300 MHz, CDCl$_3$) δ ppm: 7.8-7.75 (m, 3H), 7.5 (dd, J=2.0 Hz, J'=8.6 Hz, 1H), 7.2 (d, J=2.3 Hz, 1H), 7.15 (m, 2H), 5.7 (s, 1H), 4.3 (m, 2H), 3.65 (m, 2H), 3.4 (m, 2H), 3.05 (m, 2H), 2.85 (m, 2H), 2.3 (s, 3H).

6-(3-(2-(2-Hydroxyethylamino)ethoxy)-5-methyl-1H-pyrazol-1-yl)naphthalen-2-ol hydrochloride

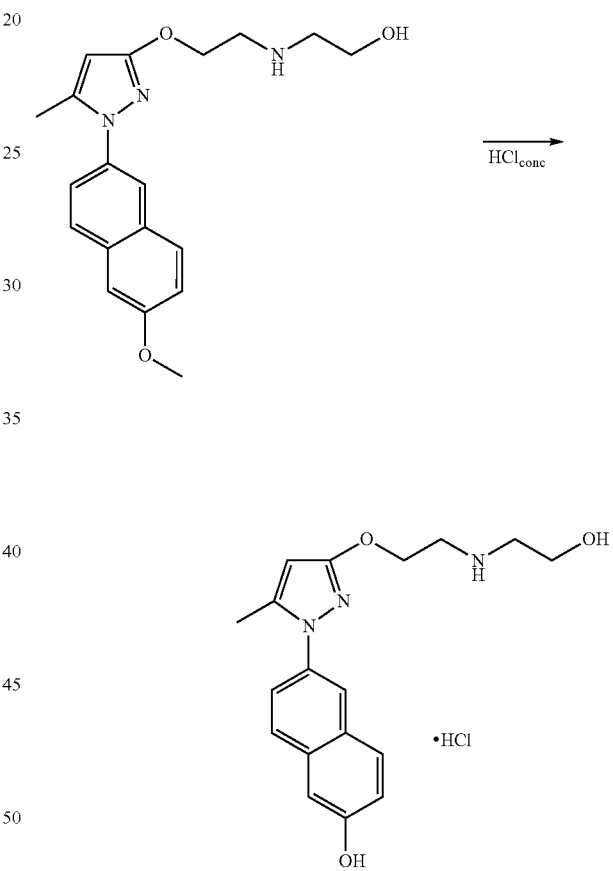

A solution of 2-(2-(1-(6-methoxynaphthalen-2-yl)-5-methyl-1H-pyrazol-3-yloxy)ethylamino)etanol (104 mg, 0.307 mmol) in HCl conc. (4 ml) was heated to reflux during 7 hrs. Then, it was cooled and evaporated to dryness in a rotavapor, the crude residue was washed with ethyl ether and 91 mg of 6-(3-(2-(2-hydroxyethylamino)ethoxy)-5-methyl-1H-pyrazol-1-yl)naphthalen-2-ol hydrochloride were obtained as a solid with a melting point=115-118° C. (yield: 81%)

Purity determined by HPLC: 97.2%

$^1$H-NMR (CD$_3$OD) δ ppm: 8.9 (bs, 2H), 7.85-7.75 (m, 3H), 7.5 (dd, J=2.2 Hz, J'=8.8 Hz, 1H), 7.2 (m, 2H), 5.85 (s, 1H), 4.4 (t, J=5.1 Hz, 2H), 3.7 (m+H$_2$O, 2H), 3.35 (m, 2H), 3.05 (m, 2H), 2.3 (s, 3H).

In the following table 2, there is listed compounds according to the invention with their corresponding mass spectrometry data.

TABLE 2

| Compound nr | Example references | Name | [M + H]+ |
|---|---|---|---|
| 1 | Example 4 | 6-(5-methyl-3-(2-morpholinoethoxy)-1H-pyrazol-1-yl)-1,2-dihydronaphthalene-1,2-diol | 372 |
| 2 | Example 1 | 4-{2-[1-(6-hydroxynaphthalen-2-yl)-5-methyl-1H-pyrazol-3-yloxy]ethyl}morpholine chlorhydrate | 354 |
| 3 | Example 2 | 4-{2-[1-(5-hydroxynaphthalen-2-yl)-5-methyl-1H-pyrazol-3-yloxy]ethyl}morpholine | 354 |
| 4 | Example 3 | 4-{2-[1-(7-hydroxynaphthalen-2-yl)-5-methyl-1H-pyrazol-3-yloxy]ethyl} morpholine chlorhydrate | 354 |
| 5 | — | 2-(2-(5-methyl-1-(naphthalen-2-yl)-1H-pyrazol-3-yloxy)ethylamino)ethanol chlorhydrate | 312 |
| 6 | — | 4-(2-(5-methyl-1-(naphthalen-2-yl)-1H-pyrazol-3-yloxy)ethyl)morpholine 4-oxide | 354 |
| 7 | — | 4-(2-(5-methyl-1-(naphthalen-2-yl)-1H-pyrazol-3-yloxy)ethyl)morpholin-2-ol | 354 |
| 8 | Example 5 | 6-(3-(2-(2-hydroxyethylamino)ethoxy)-5-methyl-1H-pyrazol-1-yl)naphthalen-2-ol hydrochloride | 327 |

Example 6

Binding Affinity Test for Sigma Inhibitors According to the Invention

Some representative compounds of the invention were tested for their activity as sigma-1 inhibitors. The following protocols were followed:

Brain membrane preparation and binding assays for the 61-receptor were performed as described (DeHaven-Hudkins et al., 1992) with some modifications. In brief, guinea pig brains were homogenized in 10 vols. (w/v) of Tris-HCl 50 mM 0.32 M sucrose, pH 7.4, with a Kinematica Polytron PT 3000 at 15000 r.p.m. for 30 s. The homogenate was centrifuged at 1000 g for 10 min at 4° C. and the supernatants collected and centrifuged again at 48000 g for 15 min at 4° C. The pellet was re-suspended in 10 volumes of Tris-HCl buffer (50 mM, pH 7.4), incubated at 37° C. for 30 min. and centrifuged at 48000 g for 20 min at 4° C. Following this, the pellet was re-suspended in fresh Tris-HCl buffer (50 mM, pH 7.4) and stored on ice until use.

The radioligand used was [$^3$H]-(+)-pentazocine at 3.0 nM and the final volume was 200 µl. The incubation was initiated with the addition of 100 µl of membrane at a final tissue concentration of approximately 5 mg tissue net weight/mL and the incubation time was 150 min. at 37° C. After incubation, the membranes were collected onto pre-treated glass fiber filter plate (MultiScreen-FC, Millipore), with polyethylenimine 0.1%. The filters were washed two times with 200 µl of washing buffer (50 mM Tris Cl, pH=7.4) and then 25 µl of Ecoscint H liquid scintillation cocktail were added. Microplates were allowed to set for several hours and then quantified by liquid scintillation spectrophotometry (1450 Microbeta, Wallac). Non-specific binding was determined with 1 µM haloperidol.

The Microbeta reader gave the counts per minute (cpm) per each well that were processed in Excel work sheet to obtain means of duplicates. The Specific Binding value was obtained subtracting Non-Specific Binding (NSB) from Total Binding (TB).

Percentages of Specific Bound for each different compound concentration were calculated from duplicates cpm means as follows:

$$\frac{Compound - NSB}{Specific\ Bound} \times 100 \qquad [\text{Equation 1}]$$

The values were used for non-linear $IC_{50}$ (nM) calculation and graph representation. Inhibition constant ($K_i$) was calculated from $IC_{50}$ according the Cheng-Prussof Equation:

$$K_i = \frac{IC_{50}}{1 + \frac{[L]}{K_d}} \qquad [\text{Equation 2}]$$

in which [L] means the radioligand concentration, determined from the experimental total counts (dpm) using the Specific Activity of the radioligand, and $K_d$ the dissociation constant of the radioligand.

The historical value of the saturation constant $K_d$ of [$^3$H]-(+)pentazocine was 3.1 nM.

References

DeHaven-Hudkins, D. L., L. C. Fleissner, and F. Y. Ford-Rice, 1992, Characterization of the binding of [$^3$H](+)pentazocine to a recognition sites in guinea pig brain, Eur. J. Pharmacol. 227, 371-378.

The binding affinities (expressed as Ki in nM) and the inhibitory concentrations (expressed as $IC_{50}$) for the compounds prepared according to the previous examples were as follows:

TABLE 3

| Compound nr. | $IC_{50}$ | Ki (nM) |
|---|---|---|
| 1 | >1,000 | — |
| 2 | >1,000 | — |
| 3 | — | 329 |
| 4 | >1,000 | — |
| 5 | — | 102.3 |
| 6 | >1,000 | — |

The invention claimed is:

1. A compound having the formula (I):

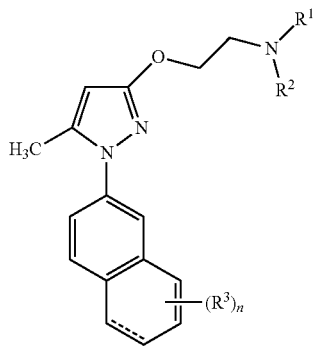

wherein the dashed line (represented by - - - ) represents an optional double bond;
R$^1$ is hydrogen and R$^2$ is hydroxyethyl;
each R$^3$ is independently hydroxy or C$_{1-6}$alkoxy;
n is selected from 0, 1, and 2;
or a N-oxide, salt or stereoisomer thereof.

2. The compound of claim 1, wherein the dashed line represents a double bond.

3. The compound of claim 1, wherein said compound has the formula (If)

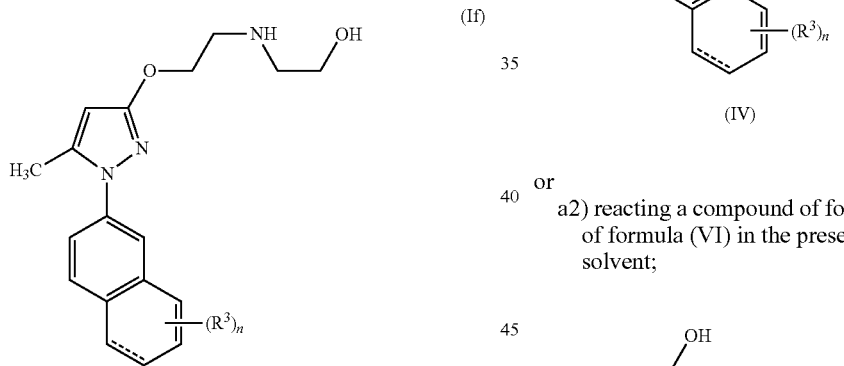

wherein the dashed line (represented by - - - ) represents an optional double bond;
each R$^3$ is independently hydroxy or C$_{1-6}$alkoxy;
n is selected from 0, 1, and 2; or
a N-oxide, salt or stereoisomer thereof.

4. The compound of claim 1, wherein said compound is selected from the group consisting of:
2-[2-(5-methyl-1-naphthalen-2-yl-1H-pyrazol-3-yloxy)-ethylamino]-ethanol;
2-(2-(1-(6-methoxynaphthalen-2-yl)-5-methyl-1H-pyrazol-3-yloxy)ethylamino)etanol;
6-(3-(2-(2-hydroxyethylamino)ethoxy)5-methyl-1H-pyrazol-1-yl)naphthalen-2-ol; and
their pharmaceutically acceptable salts and stereoisomers thereof.

5. A pharmaceutical composition comprising a pharmaceutically effective amount of a compound according to claim 1 and a pharmaceutically acceptable carrier.

6. A process for preparing a compound as claimed in claim 1, wherein said process comprises:
a1) reacting a compound of formula (II) with a compound of formula (III) in a suitable solvent, and optionally in the presence of a catalyst and an aqueous solution of alkali, to obtain compound of formula (IV), which is further reacted with compound of formula (V) in a suitable solvent;

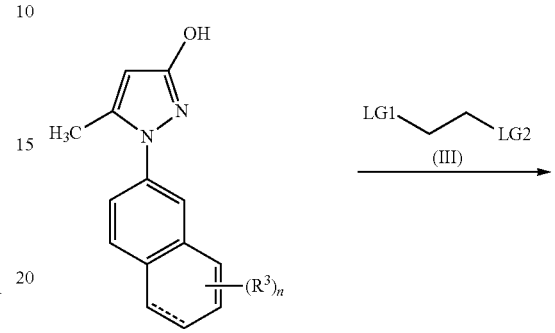

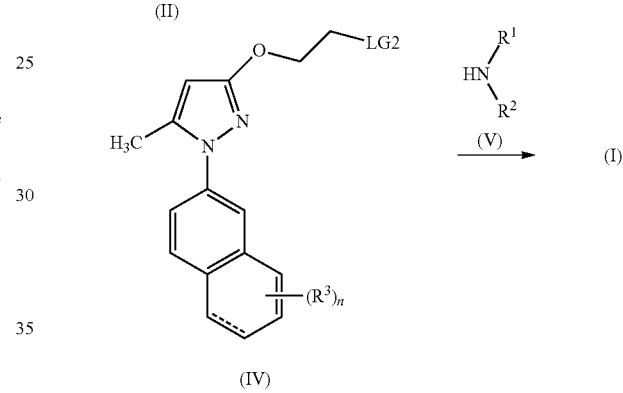

or
a2) reacting a compound of formula (II) with a compound of formula (VI) in the presence of a base and a suitable solvent;

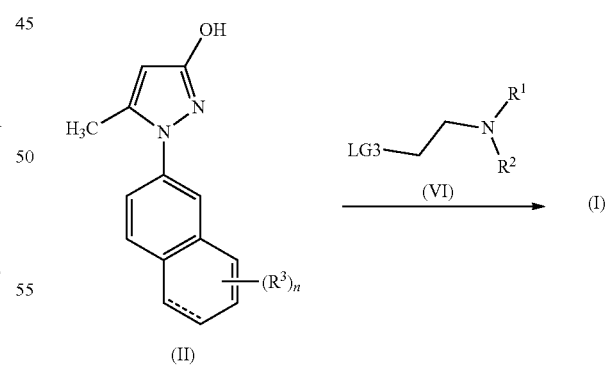

thereby obtaining compound of formula (I);
wherein in each of the compounds of formula (I), (II), (III), (IV), (V), and (VI), where applicable,
R$^1$, R$^2$, R$^3$, and n are as defined in claim 1;
LG1, LG2, and LG3 represent each a leaving group.

7. A pharmaceutical composition comprising a pharmaceutically effective amount of a compound according to claim 4 and a pharmaceutically acceptable carrier.

8. A pharmaceutical composition comprising a pharmaceutically effective amount of a compound according to claim 3 and a pharmaceutically acceptable carrier.

\* \* \* \* \*

UNITED STATES PATENT AND TRADEMARK OFFICE
CERTIFICATE OF CORRECTION

PATENT NO. : 8,492,425 B2  
APPLICATION NO. : 12/988929  
DATED : July 23, 2013  
INVENTOR(S) : Antoni Torrens Jover et al.

Page 1 of 1

It is certified that error appears in the above-identified patent and that said Letters Patent is hereby corrected as shown below:

On the Title Page

At Item 74 "Attorney, Agent, or Firm," replace "Hoffman" with --Hoffmann--.

In the Specifications

At Column 27 Lines 30-51, replace "the 61-receptor" with --the σ1-receptor--.

Signed and Sealed this  
Twenty-eighth Day of January, 2014

Michelle K. Lee  
*Deputy Director of the United States Patent and Trademark Office*